United States Patent [19]

Kafrawy et al.

[11] Patent Number: 4,470,416

[45] Date of Patent: Sep. 11, 1984

[54] COPOLYMERS OF LACTIDE AND/OR GLYCOLIDE WITH 1,5-DIOXEPAN-2-ONE

[75] Inventors: Adel Kafrawy, Rockaway; Frank V. Mattei, Piscataway; Shalaby W. Shalaby, Lebanon, all of N.J.

[73] Assignee: Ethicon, Inc., Somerville, N.J.

[21] Appl. No.: 505,160

[22] Filed: Jun. 17, 1983

[51] Int. Cl.³ .................... A61L 17/00; C08G 63/08
[52] U.S. Cl. ................................ 128/335.5; 528/354
[58] Field of Search ...................... 528/354; 128/335.5

[56] References Cited

U.S. PATENT DOCUMENTS 4,052,988 10/1977 Doddi et al. ................. 128/335.5
4,137,921 2/1979 Okuzumi et al. .............. 128/335.5
4,190,720 2/1980 Shalaby ............................. 528/354
4,273,920 6/1981 Nevin ............................. 528/354 X Primary Examiner—Earl A. Nielsen
Attorney, Agent, or Firm—Charles J. Metz

[57] ABSTRACT

Copolymers are prepared from 1,5-dioxepan-2-one and lactide and/or glycolide. The copolymers are useful in surgical applications such as sutures, suture lubricants, and allied surgical products. 1,5-Dioxepan-2-one is produced by a new process comprising first reacting ethylene glycol with an alkyl acrylate to form alkyl 3-(2-hydroxyethoxy)propionate, which is then cyclized by contacting with a trans-esterification catalyst.

9 Claims, No Drawings

COPOLYMERS OF LACTIDE AND/OR GLYCOLIDE WITH 1,5-DIOXEPAN-2-ONE

The invention relates to copolymers of 1,5-dioxepan-2-one with lactide and/or glycolide, and to a new process for making 1,5-dioxepan-2-one.

BACKGROUND OF THE INVENTION

Synthetic absorbable polymers have been used to produce various surgical products such as sutures, implants, prostheses, and the like, for several years. Illustrative U.S. patents that disclose such polymers are U.S. Pat. Nos. 3,297,033, 3,044,942, 3,371,069, 3,531,561, 3,636,956, Re. 30,170, and 4,052,988.

This invention provides a new class of synthetic absorbable polymers that have a variety of uses. The polymers are copolymers of 1,5-dioxepan-2-one with lactide and/or glycolide. The invention also provides a new method for making 1,5-dioxepan-2-one.

THE PRIOR ART

British Pat. No. 1,272,733 disclosed the preparation of 1,5-dioxepan-2-one by first reacting ethylene glycol with acrylonitrile in the presence of sodium hydroxide, to form 2-($\beta$-cyanoethoxy)ethanol. This latter compound is converted into the cyclic imino ether hydrochloride by reaction with dry HCl gas in dry methylene chloride. The imino hydrochloride was then converted into the desired cyclic ether lactone by hydrolysis. The British patent mentions that the ether lactones have utility in the production of polymers.

U.S. Pat. No. 4,190,720 (Shalaby) discloses copolymers of epsilon-caprolactone and 1,5-dioxepan-2-one, and their use in surgical applications.

U.S. Pat. Nos. 4,045,418 and 4,057,537 disclose copolymers of L(−)lactide or D,L-lactide with epsilon-caprolactone.

Rehberg et al., J. Am. Chem. Soc., 68, 544 (1946) disclose the preparation of methyl $\beta$-methoxypropionate by reacting methanol with methyl acrylate in the presence of sodium methoxide. See also J. Am. Chem. Soc., 69, 2966 (1947).

DETAILED DESCRIPTION OF THE INVENTION

Preparation of 1,5-Dioxepan-2-One 1,5-Dioxepan-2-one ("DXO") is a cyclic ether-ester of the formula:

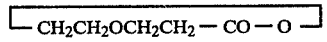  I

DXO can be prepared by the following sequence of reactions:

(a) Ethylene glycol is reacted with an approximately equivalent proportion of methyl acrylate (or other alkyl ester of acrylic acid) in the presence of alkali metal alkoxide or other suitable organometallic or organic base catalyst to produce methyl 3-(2-hydroxyethoxy)-pro-pionate:

HOCH$_2$CH$_2$OCH$_2$CH$_2$—CO—OCH$_3$   II (b) II is then neutralized by treatment with sulfonated ion exchange resin, and then filtered. The filtrate is then distilled in the presence of a trans-esterification catalyst such as tetraisopropyl orthotitanate. DXO is recovered in reasonable yield as a distillate.

This process is preferable to the known procedures that use acrylonitrile because of its simplicity and because it produces very pure product (polymerization grade) in relatively high yield.

The following is an illustration of the preparation of DXO by the new process:

EXAMPLE 1

Preparation of 1,5-Dioxepan-2-one

To a one-liter, three-necked flask equipped with a dropping funnel and condenser was added 248 grams (4.0 moles) of ethylene glycol. Four grams (0.074 mole) of sodium methoxide was stirred in the glycol, and upon dissolution, 344 grams (4.0 moles) of methyl acrylate was added dropwise. The mixture was heated at 85° C. for 17 hours, cooled to room temperature, then stirred with 150 grams of water pre-soaked Amberlite IR-120 (sulfonated ion exchange resin) overnight. The Amberlite was filtered and the filtrate was treated with 10 milliliters of tetraisopropyl orthotitanate catalyst and distilled under reduced pressure (0.05 torr). The initial fraction, boiling point ambient to 80° C., was mostly water, catalyst, and compound II. The liquid which distilled over at 80°-85° C. was chilled in dry ice and thus became very viscous. Upon trituration with anhydrous diethyl ether, white crystals of DXO formed which were quickly filtered. The crude DXO was rapidly recrystallized from anhydrous ether to give colorless crystals, mp. 35° C. DXO was stored in a dry container in a freezer.

The recovered intermediate II can be recycled by treatment with more titanate catalyst and distilled to give more DXO.

The cyclization of compound II to give DXO has been conducted with a variety of catalysts, including stannous octoate, dibutyltin oxide, and antimony trioxide.

PREPARATION OF COPOLYMER

The copolymer of the invention is produced by copolymerizing DXO with glycolide and/or lactide. The resulting copolymer will then comprise repeating divalent units of the formulas:

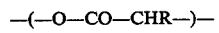   III

   IV wherein R represents hydrogen or methyl.

The copolymerization reaction is carried out in the presence of a suitable catalyst, such as an esterification catalyst, and a small proportion of an alcohol or other suitable monofunctional or difunctional initiator or precursor (to open the DXO and glycolide and/or lactide rings). While the reaction would proceed with a wide variety of such catalysts, as a practical matter because the polymers are intended for use in absorbable products, it is preferred to use biologically acceptable catalysts in small amounts. Specific examples of such catalysts are stannous octoate and dibutyltin oxide. Illustrative proportions are from about 5,000 to about 200,000, and preferably from about 10,000 to about 100,000 moles of monomer (i.e., moles of DXO plus lactide and/or glycolide) per mole of catalyst.

EXAMPLE 2

This example illustrates the preparation of the copolymer of the invention.

herein as "PG-2". It had an intrinsic viscosity of 0.57 in HFIP.

The specific reaction conditions and results are displayed below in Table II:

TABLE II

| Example No. | Monomer Charge Composition[1] DXO/GLY/PG-2 | $\frac{\text{Mnmr}^{[2]}}{1,6\text{HD}}$ | $\frac{\text{Mnmr}^{[3]}}{\text{Catalyst}}$ | Reaction[4] Conditions | % Conversion | I.V.[5] dl/gm | $T_m$[6] °C. | %[7] Crystallinity |
|---|---|---|---|---|---|---|---|---|
| 2 | 25/75/0 | 1000 | 60,000 | A | 100 | 1.34 | 215–220 | 32 |
| 3 | 30/70/0 | 1000 | 60,000 | A | 98 | 1.20 | 134–147 | 24 |
| 4 | 25/70/5 | — | 60,000 | B | 88 | 1.60 | 180–186 | 24 |
| 5 | 20/75/5 | — | 125,000 | B | 95 | 1.76 | 212–219 | 32 |
| 6 | 25/70/5 | 1000 | 125,000 | B | 100 | 1.16 | 185–210 | 24 |
| 7 | 20/75/5 | 1000 | 60,000 | B | 100 | 0.96 | 216–222 | 29 |
| 8 | 20/75/5 | 1000 | 60,000 | C | 90 | 0.70 | 204–211 | — |
| 9 | 20/75/5 | 1000 | 125,000 | D | 95 | 0.82 | 180–184 | 36 |
| 10 | 25/75/0 | 1000 | 60,000 | E | 99 | 0.47 | 158–168 | — |
| 11 | 20/75/0 | 1000 | 60,000 | E | 97 | 0.81 | 171–174 | — |
| 12 | 25/70/5 | 2000 | 60,000 | B | 99 | 0.97 | 212–216 | — |
| 13 | 20/75/5 | 2000 | 60,000 | B | 98 | 0.92 | 215–217 | — |
| 14 | 20/75/5 | 2000 | 60,000 | D | 97 | 0.89 | 162–173 | — |
| 15 | 25/75/0 | 1000 | 60,000 | F | 95 | 0.69 | 164–182 | — |

[1]Molar proportions of DXO/Glycolide/PG-2; "Moles" of PG-2 refers to the monomer units in the polyester.
[2]Moles of (DXO plus glycolide)/moles of 1,6-hexanediol initiator.
[3]Moles of (DXO plus glycolide)/moles of stannous octoate catalyst.
[4]Polymerization Procedure:
(A) Vac. sealed vessel, 100° C./0.5 hr., 150–190°/20 min., 190°/18 hr.
(B) Charge monomers, 140° C. until monomers mix, cool to 100°, add catalyst, vac. seal, 140°/0.5 hr., 190°/18 hr.
(C) Overhead stirring, 140° C. until monomers mix, cool to 100°, add catalyst, 220°/1 hr.
(D) Overhead stirring, 140° C. until monomers mix, cool to 100°, add catalyst, 215°/3 hr.
(E) Overhead stirring, 140° C. until monomers mix, cool to 100°, add catalyst, 215°/4 hr.
(F) Vac. Sealed Vessel, 100° C./0.5 hr., 150–190°/20 min., 190°/3 hr.
[5]Intrinsic viscosity in HFIP, at 25° C. and 0.1 gram/deciliter concentration.
[6]$T_m$ was determined by DSC or hot stage microscopy.
[7]% Crystallinity was determined by X-Ray analysis.

Preparation of Glycolide/Ether Lactone Copolymer

A glycolide/DXO copolymer of initial composition 75/25, mole/mole, was prepared by charging 11.25 grams (96.98 mmoles) glycolide, 3.75 grams (32.33 mmoles) DXO, 0.0153 gram (0.1293 mmoles) 1,6-hexanediol (initiator) and 0.065 milliliter of 0.033 molar stannous octoate solution in toluene (2.1×10⁻⁶ mole), to a 50 milliliter ampule. The ampule was sealed under partial vacuum and then held at 190° C. for 18 hours. Upon cooling to room temperature, an off-white, tough copolymer was obtained. The latter was ground and devolatilized at 110° C. for 16 hours under vacuum to give a copolymer with the following properties:

TABLE I

| | |
|---|---|
| I.V. (HFIP)[1] | 1.34 dl/g |
| Conversion | ~100% |
| $T_m$ (Hot stage microscopy) | 200°–220° C. |
| $T_m$ (DSC) | 215°–225° C. |
| % crystallinity (X-Ray) | 32% |
| Final Composition (Proton NMR) | 75.8% Glycolate units 24.2% DXO units |

[1]Intrinsic viscosity, tested at 25° C. and at a concentration of 0.1 gram per deciliter in hexafluoroisopropyl alcohol.

The following examples illustrate other aspects of this invention:

EXAMPLES 3–15

The general procedure described in Example 2 was followed in the preparation of several DXO/glycolide copolymers, some of which were polymerized in the presence of a polyester of ethylene glycol and 1,4-phenylene-bis-oxyacetate, and therefore formed a copolyester with said polyester. Said polyester is referred to

EXAMPLES 16–21

Several of the polymers from previous examples were extruded into monofilaments at a shear rate of 212.6 sec.⁻¹. The screw in this extruder had a L/D (length to diameter) ratio of 24:1, and the spinnerette had a diameter of 40 mils. The monofilaments were extruded into ice water. The take-up speed in all cases was 24 feet/minute (which yielded a "jet stretch" of about 2 to 3X). Table III sets forth additional extrusion conditions;

TABLE III

| Example | Example No. of polymer | Melt Temp., °C. | Apparent Viscosity of Melt, Poises |
|---|---|---|---|
| 16 | 2 | 230 | 1289 |
| 17 | 3 | 175 | 4566 |
| 18 | 4 | 220 | 2149 |
| 19 | 5 | 235 | 3653 |
| 20 | 6 | 220 | 1235 |
| 21 | 7 | 225 | 993 |

The monofilaments were then drawn, annealed at 80° C. at constant strain for 6 hours and then subjected to sterilization by ⁶⁰Co irradiation (total dose—2.5 Mrads). Table IV, below, sets forth the drawing conditions, tensile properties, and certain other properties of the monofilaments. The results of the tensile properties show three values (except for knot strength, where only one value is shown). The first is the tensile property as drawn, the second after annealing, and the third after annealing plus ⁶⁰Co sterilization. The tensile values under knot strength are for the unannealed monofilaments, only.

TABLE IV

| Example | Drawing[1] Conditions | Tensile Straight, psi × 10⁻³ | Tensile Knot, psi × 10⁻³ | Elongation, % | Young's Modulus, psi × 10⁻³ | IV in HFIP Before ⁶⁰Co | IV in HFIP After ⁶⁰Co | % Breaking Strength Retention In Vivo (Rats) After Both Annealing And ⁶⁰Co Sterilization[2] Initial | 7 Days | 14 Days |
|---|---|---|---|---|---|---|---|---|---|---|
| 16 | 5X, 53° C. | 59,62,50 | 50 | 82,32,25 | 116,420,400 | — | — | 100 | 16 | 0 |
| 17 | 4X, 50° C. plus 1.5X, 60° C. | 47,51,31 | 41 | 53,31,22 | 100,98,93 | — | — | 100 | 13 | 0 |
| 18 | 4X, 69° C. | 54,56,57 | 52 | 54,30,31 | 570,900,845 | 1.15 | 0.97 | 100 | 33 | 0 |
| 19 | 4X, 76° C. | 59,63,58 | 58 | 45,27,43 | 752,961,932 | 1.20 | 0.98 | 100 | 35 | 0 |
| 20 | 5X, 85° C. | 35,30,32 | 35 | 42,36,29 | 296,500,215 | — | — | 100 | 30 | 0 |
| 21 | 5X, 78° C. | 59,49,49 | 57 | 37,24,28 | 670,836,526 | — | — | 100 | 33 | 0 |

[1]Draw ratio, Temperature.
[2]The monofilaments were implanted in the gluteal muscle of rats, and were removed after the designated periods of time to determine their breaking strengths.

In several of the foregoing Examples, the moiety

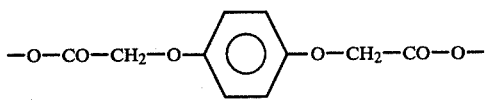

was incorporated in the polymers of the invention by carrying out the polymerization in the presence of a polyester of ethylene glycol and 1,4-phenylene-bis-oxyacetate. When this is done, an ester interchange reaction occurs and the resulting copolyester contains DXO, glycolic acid, ethylene glycol, and 1,4-phenylene-bis-oxyacetate residues. The reason for doing this is that the phenylene-bis-oxyacetate moieties improve the resistance of the polymer to irradiation such as gamma rays. Instead of the phenylene-bis-oxyacetate moieties, other moieties which impart resistance to irradiation may also be employed by similar procedures. Examples of other moieties which can impart resistance to irradiation include the moiety

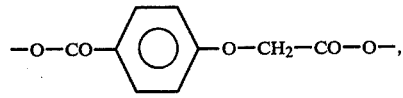

derived from 4-carboxymethoxybenzoic acid.

EXAMPLES 22–23

Two glycolide/DXO copolymers were dissolved in 1,1,2-trichlorethane to give solutions containing 10–11 weight percent polymer. Several lengths of size 2/0 dyed "Vicryl" lactide/glycolide copolymer braid were immersed in the solution for 20–40 seconds, removed, the excess coating was wiped off, and the braid was dried. Pick-up or % add-on was determined by weighing before and after coating. Both solutions were then diluted to 5–6 wt/wt % solids using 1,1,2-trichlorethane. The coating process was repeated with several lengths of a new batch of "Vicryl" braid. The trichloroethane used as a solvent here is only one of several organic solvents that can be used.

As may be seen from the results set forth in Table V, both copolymers have good dry tie-down smoothness (compared to a zero rating for uncoated "VICRYL"), while one copolymer (50/50 molar ratio) showed reasonably good tie-down even when wet. This would probably also improve the snuggability of a square knot; past experience has shown that tie-down smoothness and snuggability go hand-in-hand. Previous experience has shown repeatedly that some fibers require different levels of add-on to give an improvement in tie-down smoothness, and it is quite likely that some braids may require much lower add-on levels to show significant improvements in smoothness. Routine experimentation will suffice to determine the optimum add-on in particular cases.

TABLE V

| Glycolide/DXO* Molar Ratio: | 40/60 | 50/50 | 40/60 | 50/50 |
|---|---|---|---|---|
| Solution Concentration, Wt. % Solids | 10–11 | 10–11 | 5–6 | 5–6 |
| Solution Clarity | Clear | Hazy | Clear | Clear |
| % Pick-Up or Add-on, Dry Basis | 9 | 9 | 5 | 6 |
| Smoothness of Tie-Down, Subjective-Manual** Dry | 8 | 9 | 7 | 8 |
| Smoothness of Tie-Down, Subjective-Manual** Wet | 4 | 7 | 3 | 6 |
| Appearance of Coated Braid | All Very Good | | | |

*Glycolide/DXO = Glycolide/1,5-dioxepan-2-one molar ratio
**On a scale of 0–10 in the subjective tie down, 0 is the roughest (uncoated VICRYL) while 10 is the smoothest. This is generally a very accurate and reproducible test.

A preferred method of applying the coating would be to continuously pull the braid to be coated through a trichloroethane solution of the copolymer upward in a vertical direction to insure uniform drainage. The freshly coated fiber would then be pulled continuously through a drying tunnel, taken up on a wind-up wheel, and the drying process completed by drying in vacuum overnight at room temperature. However, other conventional coating procedures can be used, if desired.

An ideal application of this coating is on braided sutures, since they generally have a chattery or rough tie-down. The coating is particular useful on absorbable braids, since the coating is itself absorbable. Absorbable monofilaments would probably also benefit from the coating. These applications could easily be extended to non-absorbable braids and mono-filaments. Absorbable materials include lactide and glycolide homopolymers and copolymers, poly-p-dioxanone, catgut, collagen, polyvinyl alcohol, etc. Non-absorbable sutures include polyester, polypropylene, nylon, silk, cotton, linen, and the like.

Broadly speaking, the proportion of DXO to glycolide and/or lactide in the copolymer has not been found to be narrowly critical. For certain end-use applications, however, more narrowly defined ranges of proportions have been found to be preferred. For instance, when the copolymer is intended for the production of strong fibrous structures (such as sutures), it is preferred to employ the DXO in proportions of from about 3 to about 33 mole percent, based on moles of DXO plus glycolide and/or lactide. When the copolymer is intended for use as a lubricant for a suture, then the preferred proportions of DXO will be within the range of from about 40 to about 80 mole percent, on the same basis.

While the utility of this copolymer has been most particularly illustrated by the production of sutures and suture lubricants, the copolymer can also be used to produce hemostatic clips, bone wax sealants, and other surgical materials and devices.

What is claimed is:

1. A copolymer which comprises the repeating divalent units of the formulas:

—(—O—CO—CHR—)— and
—(—O—CO—CH$_2$CH$_2$OCH$_2$CH$_2$—)— wherein R represents hydrogen or methyl.

2. The copolymer of claim 1 wherein the divalent unit of the formula —(—O—CO—CH$_2$CH$_2$OCH$_2$CH$_2$—)— constitutes from about 3 to about 33 mole percent of the copolymer.

3. A fiber comprising the copolymer of claim 2.

4. A sterile surgical suture comprising the fiber of claim 3.

5. The sterile suture of claim 4 attached at at least one end thereof to a sterile surgical needle.

6. The copolymer of claim 1 wherein the divalent unit of the formula —(—O—CO—CH$_2$CH$_2$OCH$_2$CH$_2$—)— constitutes from about 40 to about 80 mole percent of the copolymer.

7. A sterile suture containing a coating of the copolymer of claim 6 as a lubricant.

8. The sterile suture of claim 7 wherein said suture is braided.

9. A surgical device comprising the copolymer of claim 1.

* * * * *